US010213130B2

(12) United States Patent
Meredith

(10) Patent No.: US 10,213,130 B2
(45) Date of Patent: Feb. 26, 2019

(54) COMPRESSABLE CATHETER TIP WITH IMAGE-BASED FORCE SENSING

(75) Inventor: Glenn A. Meredith, Freehold, NJ (US)

(73) Assignee: Siemens Healthcare GmbH, Erlangen (DE)

(*) Notice: Subject to any disclaimer, the term of this patent is extended or adjusted under 35 U.S.C. 154(b) by 1408 days.

(21) Appl. No.: 13/547,397

(22) Filed: Jul. 12, 2012

(65) Prior Publication Data

US 2014/0018665 A1    Jan. 16, 2014

(51) Int. Cl.
*A61B 5/05* (2006.01)
*A61B 5/055* (2006.01)
*A61M 25/01* (2006.01)
*A61B 5/06* (2006.01)
*A61B 5/00* (2006.01)
A61M 25/00 (2006.01)
A61B 18/14 (2006.01)
A61B 90/00 (2016.01)
A61B 34/20 (2016.01)

(52) U.S. Cl.
CPC .............. *A61B 5/055* (2013.01); *A61B 5/064* (2013.01); *A61B 5/6852* (2013.01); *A61B 5/6885* (2013.01); *A61M 25/0127* (2013.01); A61B 18/1492 (2013.01); A61B 90/39 (2016.02); A61B 2034/2051 (2016.02); A61B 2090/065 (2016.02); A61B 2090/374 (2016.02); A61M 25/0069 (2013.01); A61M 25/0074 (2013.01); A61M 2025/0166 (2013.01)

(58) Field of Classification Search
CPC ........ A61B 18/1492; A61B 2034/2051; A61B 2090/065; A61B 2090/374; A61B 5/055; A61B 5/064; A61B 5/6852; A61B 5/6885; A61B 90/39
See application file for complete search history.

(56) References Cited

U.S. PATENT DOCUMENTS

| 5,211,165 | A | 5/1993 | Dumoulin et al. |
| 5,255,679 | A | 10/1993 | Imran |
| 7,311,704 | B2 | 12/2007 | Paul et al. |
| 2005/0165301 | A1* | 7/2005 | Smith et al. .................. 600/421 |
| 2009/0076594 | A1* | 3/2009 | Sabaria ........................ 623/1.34 |
| 2009/0093806 | A1* | 4/2009 | Govari et al. .................. 606/34 |
| 2009/0171196 | A1* | 7/2009 | Olson et al. .................. 600/426 |
| 2009/0203989 | A1* | 8/2009 | Burnside et al. ............ 600/409 |
| 2010/0121269 | A1 | 5/2010 | Goldenberg et al. |
| 2010/0312095 | A1* | 12/2010 | Jenkins et al. ................ 600/411 |
| 2011/0201923 | A1* | 8/2011 | Shen .................. A61B 19/5244 600/424 |
| 2012/0323111 | A1* | 12/2012 | Jain et al. ..................... 600/411 |

OTHER PUBLICATIONS

Rea et al., "System for 3-D Real-Time Tracking of MRI-Compatible Devices by Image Processing", IEEE, Jun. 2008, vol. 13, No. 3, pp. 379-382.*

(Continued)

*Primary Examiner* — Christopher Cook

(57) ABSTRACT

A catheter (10) comprising a catheter tip (14) that is adapted to have deflection of an associated spring (22) detected by imaging techniques and to have that deflection be translated into an estimation of the tip (14) contact force.

21 Claims, 4 Drawing Sheets

(56) References Cited

OTHER PUBLICATIONS

Y. Yang, "Atrial Fibrillation Ablation, The emerging role of stereotaxis", University of California Davis Medical Center, Department of Internal Medicine, Division of Cardiovascular Medicine, 2011, http://www.ucdmc.ucdavis.edu/internalmedicine/cardio/pdf/atrial%20fibrillation%20ablation%202011.pdf.

K. Yokoyama, H. Nakagawa, D.C. Shah, et al., "Novel Contact Force Sensor Incorporated in Irrigated Radiofrequency Ablation Catheter Predicts Lesion Size and Incidence of Steam Pop and Thrombus", Circulation: Arrhythmia and Electrophysiology, 2008, pp. 354-362, vol. 1, American Heart Association.

B. Schmidt, et al., "TOCCATA Multi-Center Clinical Study: Irrigated RF Ablation Catheter with an Integrated Contact Force Sensor—Long-term Results", Heart Rhythm 2010, 2010, PO2-59, Heart Rhythm Society.

P. Polygerinos, A. Ataollahi, T Schaeffter, et al., "MRI-Compatible Intensity-Modulated Force Sensor for Cardiac Catheterization Procedures", IEEE Transactions on Biomedical Engineering, Mar. 2011, pp. 721-726, vol. 58 (No. 3).

C. L. Dumoulin, S.P. Souza, and R.D. Darrow, "Real-time position monitoring of invasive devices using magnetic resonance", Magnetic Resonance in Medicine, 1993, pp. 411-415, vol. 29.

L. Pan, J. Barbot, S. M. Shea, et al., "An Integrated System for Catheter Tracking and Visualization in MR-Guided Cardiovascular Interventions", The International Society for Magnetic Resonance in Medicine 2011, 2011, abstract 195, oral presentation.

C. McGann, et al, "Dark Regions of No-Reflow on Late Gadolinium Enhancement Magnetic Resonance Imaging Result in Scar Formation after Atrial Fibrillation Ablation," J Am Coll Cardio, 2011, pp. 177-185, vol. 58, No. 2.

J. Barbot, T. Wech, S. Shea, et al., "Accurate Localization of Active Devices during Interventional MR Imaging", The International Society for Magnetic Resonance in Medicine 2011, 2011, p. 1747.

J. Barbot, S. Shea, K. Kirchberg, et al., "Accurate Localization of Active Devices using Multi-scale Analysis for Interventional MR Imaging", The International Society for Magnetic Resonance in Medicine 2012, 2012, p. 5908.

\* cited by examiner

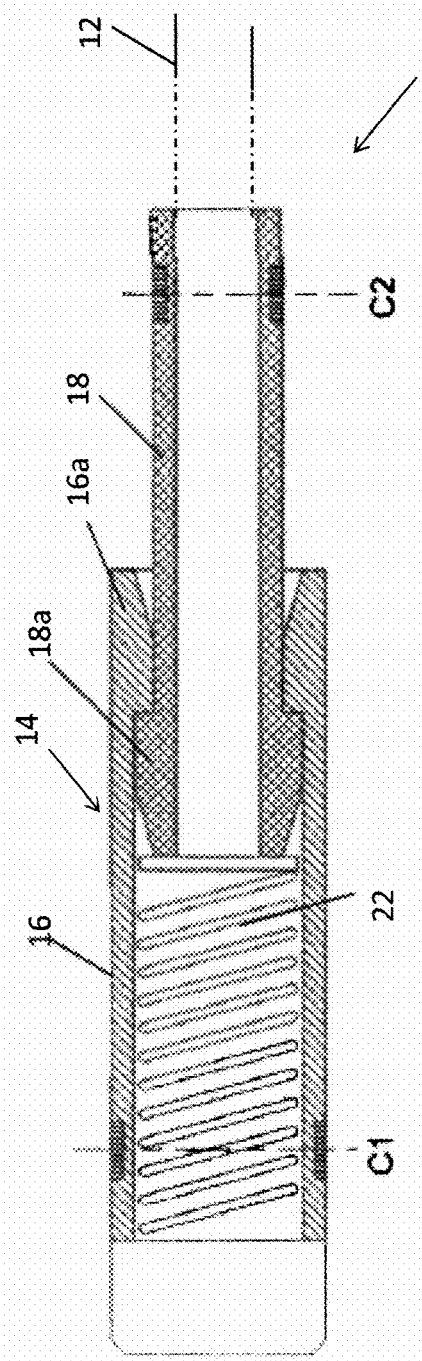
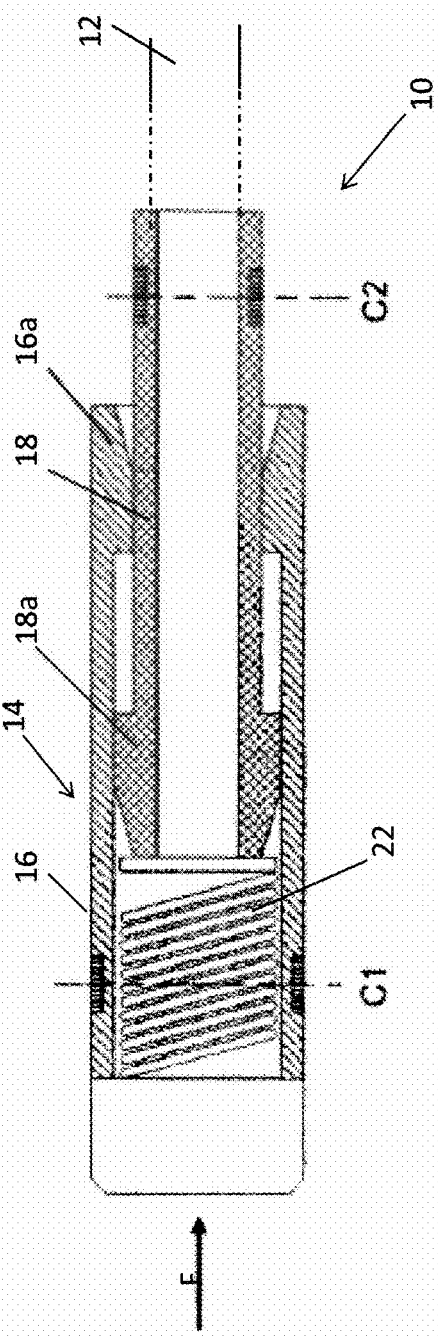
Figure 1
Figure 2

COMPRESSABLE CATHETER TIP WITH IMAGE-BASED FORCE SENSING

FIELD OF THE INVENTION

This invention generally relates to catheters and, more particularly to, catheters used for ablation procedures.

BACKGROUND OF THE INVENTION

Catheters are medical devices in the form of hollow flexible tubes for insertion into a part of the body usually to permit the passage of fluids or keep open a passageway. A catheter is normally accompanied with accessory components such as a control handle, catheter tips, surgical tools, etc., depending upon the application (and thus as a whole may be referred to, more properly, as a catheter system). In minimally invasive medical procedures, catheters are often used to deliver therapy in such a way that requires a respective catheter tip to be in contact with the tissue being treated. Radio frequency ablation (RFA) is one example of such a procedure, wherein the therapy is carried out with an ablation catheter having a tip that delivers high frequency alternating current so as to cause heating of the tissue.

While some RFA procedures involve placing the ablation tip inside the tissue to be treated, such as in the treatment of tumors, others involve only touching the ablation tip directly against the tissue surface, such as in the treatment of cardiac arrhythmias. In the latter type of procedure, where the tip only touches the tissue surface, without penetrating the tissue, the success of the procedure is partly dependent on how forcefully the ablation tip contacts the tissue surface. If the tip is not in good contact with the tissue surface, the heating therapy will be diminished. If the tip is firmly contacting the tissue surface with some force, as opposed to just lightly contacting the surface, the heating therapy will be more effective.

In the case of an RFA procedure in cardiac electrophysiology (EP), the goal is to have the RFA heat the tissue to the point of causing lesions that will block certain electrical pathways in the heart tissue that are contributing to the arrhythmia. Consequently, the degree of contact of the ablation tip against the tissue is highly important in the success of the therapy. To effectively block the electrical signal the lesions should have some depth within the tissue, as opposed to just being formed in a thin layer of the tissue surface. The depth of the lesion depends on both the contact force and the ablation power supplied to the tip. If lesions of sufficient depth and area are not being formed, because of insufficient contact and/or power, the RFA procedure will tend to be much longer and there will be a higher probability that the procedure will not be successful in stopping the arrhythmias, such that a follow-up procedure will be needed. Conversely, if there is too much force and/or too much power there are potential risks including penetration of the tissue wall, esophageal injury, cardiac tamponade or perforations from steam pops (particularly during irrigated ablation procedures at high power) (this is noted in further detail in a presentation by Y. Yang, entitled "Atrial Fibrillation Ablation, The emerging role of stereotaxis", University of California Davis Medical Center, Department of Internal Medicine, Division of Cardiovascular Medicine, 2011, http://wvvw.ucdmc.ucdavis.edu/internalmedicine/cardio/pdf/atrial%20fibrillation%20ablation%202011.pdf). Thus, successful cardiac RFA therapy seeks to form effective lesions while still minimizing the risk of complications. Both are dependent upon controlling the degree of contact of the ablation tip against the tissue.

RFA procedures are routinely performed under image guidance (usually fluoroscopy or ultrasound). While image guidance systems and techniques can provide visualization of the catheter tip, and sometimes localization of the tip within some coordinate space, the challenge is often in relating that tip information to the actual location of the anatomy of interest. Sometimes this might be accomplished by using optimal imaging planes that clearly show both the anatomy and the device, although this can be difficult in a complex anatomy such as the heart. In the case of the heart, this is further complicated by the heart beating motion, patient breathing motion and catheter motion. Other techniques involve the use of pre-acquired volumetric imaging data or 3D models of the anatomy superimposed with the real-time imaging, but these may also have inaccuracies due to registration errors stemming from the local motions, as well as from more global patient shifts. Thus, using imaging techniques alone, it can be very difficult to definitively judge whether an ablation tip is in good or appropriate contact with the tissue surface or not.

In current practice there are several means of assessing whether a good ablation is being achieved at a certain instance. While the user has some feel of the resistance as the catheter is navigated towards the target anatomy, once at the target there usually isn't enough sensitivity for the user to tell how good the contact is between the ablation tip and the tissue surface. Many catheter systems and methods for measuring tip contact force rely on some form of sensor built into the tip, such as fiber optic force sensors, piezoelectric strain gauges or other such devices. Some systems relay signals (electric, optical or fluid-based) back to the catheter's hand control, translating that signal into a corresponding force in attempt to give a truer tactile feedback to the user. Other systems provide quantitative measures which can be displayed to the user to help gauge the force of the tip contact.

In a cardiac EP system the catheters also have electrodes which measure the electrical impedance of the heart tissue, as part of a mapping function for planning where to ablate and also for checking for changes during the RFA procedure. The lesion formation is affected by important relationships between the tissue impedance and the power delivered to the ablation tip. The tissue impedance measurement also can give some indication of the tip contact, as the impedance will be increased when the tip is in good contact with the tissue.

In terms of actual catheter tip contact force, various studies use different levels to characterize their results. Although derived from cardiac perspectives, some general guidelines are offered by the Yang presentation noted above and an article by K. Yokoyama, H. Nakagawa, D. C. Shah, et al., entitled "Novel Contact Force Sensor Incorporated in Irrigated Radiofrequency Ablation Catheter Predicts Lesion Size and Incidence of Steam Pop and Thrombus", Circulation: Arrhythmia and Electrophysiology, 2008, pp. 354-362, Vol. 1, American Heart Association. An example of characterizing force levels may be described as follows:

<10-15 g low contact force, ablation ineffective
20-25 g medium contact force
>40-60 g high contact force
>100 g at risk of perforation of cardiac tissue With respect to cardiac RFA applications, however, the tip contact force must be considered along with power, impedance and temperature when attempting to achieve optimal lesions. Duration of a particular ablation is another important factor in lesion formation, with various techniques being used, ranging from short intermittent ablations at individual points to long sustained ablations where the tip may be dragged over an area for a minute or more. In this aspect, the consistency of the tip contact force is another important factor.

Several companies currently have force-sensing ablation catheters in clinical trials, including the TactiCath from Endosense and the Thermocool Smarttouch from Biosense Webster. The TactiCath uses a fiber-optic based force sensor. The SmartTouch uses magnetic signal based force sensors. Neither of these catheters are compatible with magnetic resonance imaging (MRI), but their use in various studies and clinical trials do offer evidence of the clinical benefits of having a force sensing capability (this is detailed further in the Yokoyama article noted above and an article by B. Schmidt, et al., entitled "TOCCATA Multi-Center Clinical Study: Irrigated RF Ablation Catheter with an Integrated Contact Force Sensor—Long-term Results", Heart Rhythm 2010, 2010, PO2-59, Heart Rhythm Society). The ability to perform, for example, RFA procedures, under MRI would be desirable for enhanced image guidance since, among other reasons, MRI provides superior soft tissue contrast in images and an ability to track devices in 3D space. Work is being done on MRI-compatible force-sensing catheters at King's College London, which use fiber-optic based force sensing (this is described in more detail in an article by P. Polygerinos, A. Ataollahi, T Schaeffter, et al., entitled "MRI-Compatible Intensity-Modulated Force Sensor for Cardiac Catheterization Procedures", IEEE Transactions on Biomedical Engineering, 2011 March, 58(3), pp 721-726). A completely different force-sensing approach is offered in the Stereotaxis Remote Magnetic Navigation System (detailed in the Yang presentation noted above) which claims "soft and consistent tissue contact" as one of its benefits. While using magnetics to control the catheter movement, this system is not MRI-compatible and instead is usually integrated with a fluoroscopy system.

Work is also ongoing in the area of MRI-compatible ablation catheters (for example, MRI Interventions (formerly SurgiVision) in collaboration with Siemens; Philips; Imricor in collaboration with GE; and at various research institutions, although all of these efforts are still in preclinical phases. None of these efforts publicly mention force-sensing capability as part of their MRI-compatible catheter work. The challenges of making a catheter MRI-compatible are compounded by the multiple functions required (delivery of ablation energy, measurement of impedance, measurement of tracking coil signals, etc.). While a force-sensing tip would offer clinical benefits, the addition of that capability in an MRI-compatible catheter would further complicate the design.

SUMMARY OF THE INVENTION

The present invention obviates the above problems by providing a catheter comprising a compressible catheter tip having a plurality of markers that are adapted to permit an associated image guidance system to track the markers, to obtain positional information of the markers, and to estimate contact force of the tip from the positional information. The markers may be adapted to permit the associated image guidance system to measure a deflection of the tip for estimating contact force of the tip. Alternatively, the compressible catheter tip may further have a compression spring incorporated therein and the markers may be adapted to permit the associated image guidance system to measure a deflection of the compression spring for estimating contact force of the tip.

The markers may comprise magnetic resonance tracking coils incorporated in the structure of the tip. Alternatively, the markers may comprise magnetic resonance tracking coils incorporated in the structure of the tip and the image guidance system may perform magnetic resonance imaging to track the coils and to obtain 3D positional information of the coils. The markers may also comprise passive markings on an exterior surface of the tip. Alternatively, the markers may comprise passive markings on an exterior surface of the tip and the image guidance system may perform projection imaging to track the markings and to obtain 2D positional information of the markings.

The present invention also provides a system that integrates a catheter system and an image guidance system, comprising a compressible catheter tip having a plurality of markers that provide localization of a catheter tip for visualization and navigation by the imaging guidance system and provide a measure of a deflection of the catheter tip for estimating tip contact force by the imaging guidance system. The markers may comprise magnetic resonance tracking coils incorporated by the structure of the catheter tip and the image guidance system may comprise a magnetic resonance imaging system. Alternatively, the compressible catheter tip may comprise two sections slidably connected to one another, and each having a magnetic resonance tracking coil, and a compression spring connected between the two sections and the image guidance system may derive 3D coordinates from tracking coil signals to determine the distance between the two coils and estimate tip contact force from an amount of compression of the spring.

The markers may also comprise passive markings on an exterior of the catheter tip and the image guidance system performs projection imaging. Alternatively, the compressible catheter tip may comprise two sections slidably connected to one another, and each having at least one passive marking on the respective surface, and a compression spring connected between the two sections, and the image guidance system may derive 2D coordinates from the passive markings to determine the distance between the two markings and estimate tip contact force from an amount of compression of the spring. Alternatively, the compressible catheter tip may comprise two sections slidably connected to one another, one section having a passive marking on a respective surface and the other section having at least two passive markers on a respective surface, and a compression spring connected between the two sections and the image guidance system may derive 2D coordinates from the passive markings to determine the distance between a marking on one section and a marking on the other section and estimate tip contact force from an amount of compression of the spring. In such case, the at least two passive markers on the other section may have a respective fixed and predetermined distance between a respective pair.

The present invention also provides a method of measuring the contact force exerted by a catheter tip against a target object, comprising deriving respective positional coordinates of each of a plurality of markers on the catheter tip during operation of the catheter tip; determining the respective distance between the markers during operation of the catheter tip; and calculating contact force of the tip against the target object, said catheter being adapted to provide a variable distance between at least two of the plurality of markers during operation of the catheter tip. The catheter may comprise an associated compression spring to provide said variable distance between at least two of the plurality of markers during operation of the catheter tip and the calculating step may then comprise calculating contact force of the tip against the target object based on the spring properties. The deriving step may comprise obtaining respective 3D coordinates of each of the plurality of markers from real-time localization and visualization from magnetic resonance imaging of the catheter tip and the markers. Alternatively, the deriving step may comprise obtaining respective 2D coordinates of each of the plurality of markers from real-time localization and visualization from projection imaging of the catheter tip and the markers.

The present invention also provides a method of magnetic resonance (MR) imaging guidance of a medical interventional procedure, comprising localizing MR tracking coils incorporated in a catheter used in a respective procedure and measuring catheter tip force from the localization information during MR image visualization of the patient anatomy under examination. The catheter may be adapted to provide a variable distance between at least two of the MR tracking coils during the respective procedure. The method of MR imaging guidance may further comprise presenting force measurement for the respective procedure that incorporates information as to the confidence of the localization information so as to give an indication of the accuracy of the force measurement.

BRIEF DESCRIPTION OF THE DRAWINGS

For a better understanding of the present invention, reference is made to the following description of exemplary embodiments thereof, and to the accompanying drawings, wherein:

FIG. 1 is an illustration of a cross-section of a catheter constructed in accordance with the present invention;

FIG. 2 is another illustration of the cross-section of FIG. 1;

DETAILED DESCRIPTION

Figure 3:
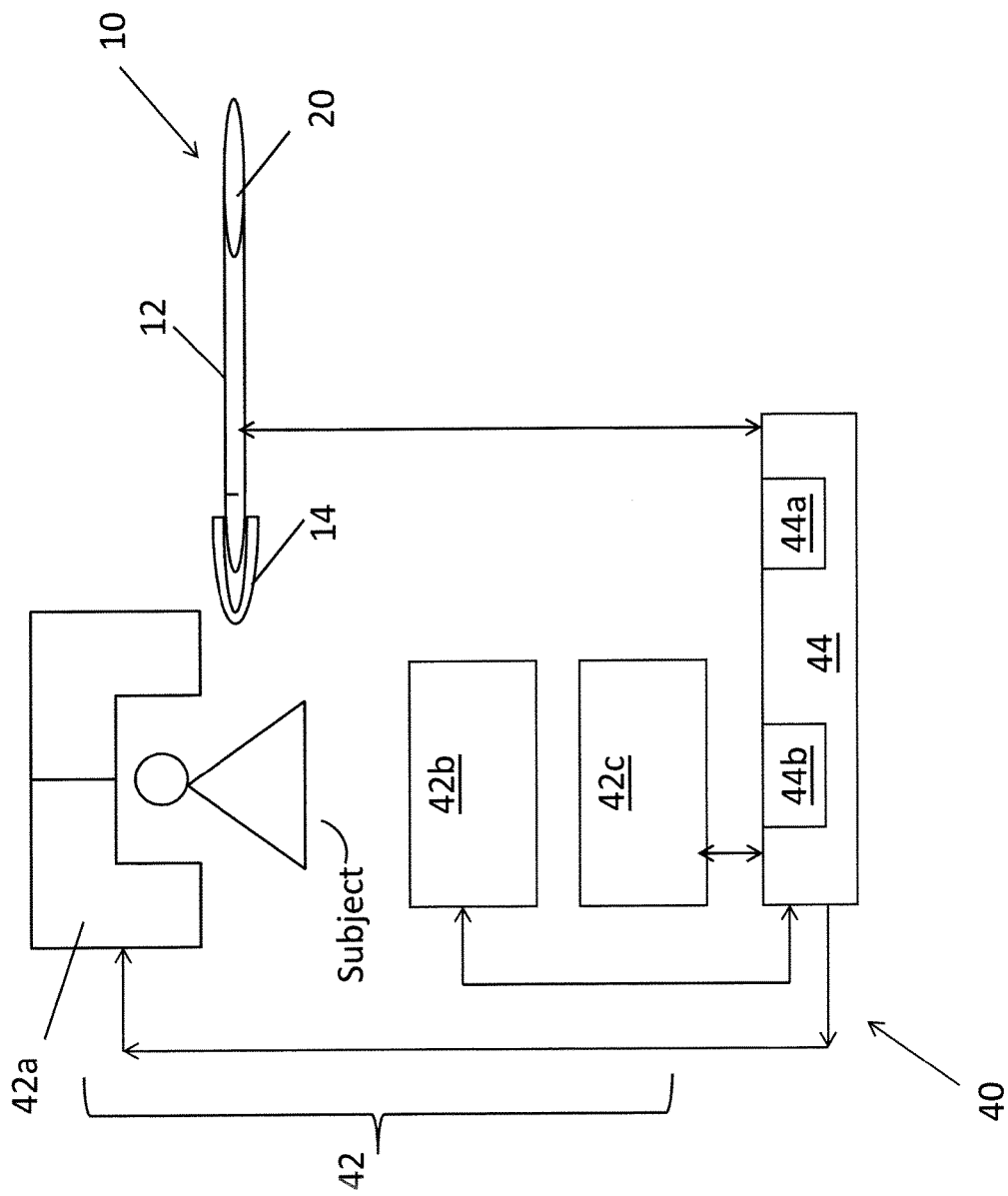
FIG. 3 is the catheter of FIG. 1, integrated with an MRI system, that provides force-sensing capability (simplified)

FIG. 1 is an illustration of a catheter 10 comprising a catheter shaft 12 that is formed as a flexible hollow tube. The shaft 12 may be constructed, for example, of a flexible polymer tubing (such as the Pebax brand) or any other material that may be used for medical applications. The catheter 10 also comprises a compressible catheter tip 14 that is attached to the end of the shaft 12 to be inserted in a patient's body. The tip 14 has two main sections, a rigid distal tip section 16 which includes, for example, an ablation tip and a rigid proximal tip section 18 which is fixed to the catheter shaft 12. The two sections 16, 18 generally follow the form of the shaft 12 and are generally tubular. Further, the two sections 16, 18 are configured and dimensioned so that the distal tip section 16 is interlocked with the proximal tip section 18 and the distal tip section 16 is adapted to freely slide back and forth over the proximal tip section 18, within certain limits. The proximal tip section 18 is fixed to the shaft 12, for example, by means of an adhesive in conjunction with the shaft 12 being passed and securely fit into the hollow of the proximal tip section 18, such that the tip 14 would not be removeable from the shaft 12. The two sections 16, 18 may be constructed, for example, of rigid polymer, or other material that may be used for medical applications.

The interlocking of the two sections 16, 18 may be accomplished via the design of the two elements in several ways. FIG. 1 in particular shows the distal tip section 16 formed to be slightly larger than the proximal tip section 18. The figure also shows that the distal end of the proximal tip section 18 having a tapered lip 18a that provides a snap fit when the proximal tip section 18 is assembled into the distal tip section 16 which has a corresponding tapered sleeve 16a at its proximal end. The snap fit is such that once assembled the sections 16, 18 will not come apart with any normal forces expected to be exerted on the distal tip section 16 away from the proximal tip section 18 in the intended applications of the catheter 10.

The catheter 10 also comprises a compression spring 22 that is mounted inside the distal tip section 16, having a first end at the proximal end of the distal tip section 16, contacting the distal end of the proximal tip section 18, and a second end at the end of the distal tip section 16 opposite its proximal end, contacting an inside end wall of the distal tip section 16. The spring 22 is mounted in a manner such that the spring 22 becomes compressed against the proximal tip section 18 when force is exerted on the tip 14 causing the distal tip section 16 to be moved towards the proximal tip section 18 along the sliding or longitudinal axis. Note that the proximal tip section 18 and the distal tip section 16 together form an assembly (i.e., a compressible catheter tip assembly 14) which will vary in length depending on the degree of deflection, extension or compression, (in its longitudinal axial direction), but will remain rigid in terms of having minimal flex of its longitudinal axis.

The distal tip section 16 and the proximal tip section 18 may each have an RF microcoil C1, C2 incorporated into their respective outer wall. As shown in FIG. 1, the microcoils C1, C2 may be configured to be annular or substantially annular. More broadly, however, each microcoil C1, C2 may be configured to generally follow the shape of the outside wall of the respective section 16, 18. Also, each section 16, 18 may have more than one microcoil in some circumstances. As will be described in more detail below, the microcoils C1, C2 function as trackers of the catheter tip 14 during image guidance and enable force-sensing by the tip 14. Note that the shaft 12 may typically include other tracking coils along its length but these would not enable force-sensing as is possible with microcoils C1, C2. Note also that the tip 14 may include other components (not shown for ease of visualization), such as electrodes for an ablation catheter.

FIG. 1 shows the compressible spring 22 in its "home state", i.e., having no contact force F at the tip 14. FIG. 2 shows the compressible spring 22 in its "maximum compression state", i.e., having contact force F at the tip 14 that causes the spring 22 to be fully compressed. Note, however, the spring 22 is mounted in a manner such that, even if the spring 22 is in its "home state", there will be some deflection in the spring 22 exerting a force on the distal tip section 16 away from the proximal tip section 18. This deflection will move the distal tip section 16 axially to the point that the tapered lip on the proximal tip section 18 catches the corresponding sleeve on the inside of the distal tip section 16. This design assures that the two sections 16, 18 are firmly held in place in the "home state" of the spring 22, with a fixed distance between the two microcoils C1, C2 in that "home state".

Note that the spring constant, k, will be such that the spring 22 will be at the midpoint of its deflection or compression range under a force equivalent to the optimal tip contact force (e.g., 25 grams) and the spring 22 will be at its maximum compression under a force which is considered to be excessive (e.g., 75 grams). Also note that different versions of the compressible tip 14 could be produced with different springs 22, and/or different spring constants, so as to optimize the deflection characteristics for certain applications and procedures which may require that more or less force is exerted.

FIG. 3 is a simplified illustration of the catheter 10 (such as an ablation catheter) that provides force-sensing capability integrated with an image guidance system 40. Advantageously, the catheter 10 is also adapted to be MRI-compatible so the image guidance system 40 may be a magnetic resonance imaging system. As described above, the catheter 10 comprises the catheter shaft 12, the compressible tip 14, and a control handle 20.

The MRI system 40 comprises a magnetic resonance (MR) scanner 42 that has a main magnet 42a, a gradient coil system 42b, and an RF system 42c. The main magnet 42 generates a strong static magnetic field in an imaging region where the subject (i.e., patient) is introduced in order to polarize the atoms of the target tissue area under examination. The gradient coil system 42b generates a time-varying linear magnetic field gradient in respective spatial directions, x, y and z, and spatially encodes the positions of the polarized or excited atoms. The RF system 42c transmits a series of RF pulses to the target tissue area to excite the "ordered" atoms and may also be adapted to switch between a transmission mode and receiver mode.

The MRI system 40 also comprises a control or computer system 44 that has a measurement and reconstruction processor 44a and a control processor 44b. The computer system 44, via the control processor 44b, controls the operation of the MR scanner 42 and its components, and, in particular, coordinates the various components to carry out a desired MR image pulse sequence. The MR scanner 42 repeats the MR image pulse sequence a number of times so the atoms oscillate around the polarized alignment direction (along the main magnetic field) during the excited state caused by the energy of RF pulses. The atoms release the RF energy, i.e., generate an RF signal, during the resonance or oscillation and as the atoms return to their respective alignments. The RF system 42c receives or detects the released RF energy and generates spatially-coded MR signals to the computer system 44. The computer system 40, by implementing appropriate reconstruction algorithms via the measurement and reconstruction processor 44a, processes the MR signals to transform them into a visual representation of the target tissue region (i.e., reconstructed MR images) for display, storage, image processing, and/or other usage.

The catheter 10 is operably connected to the MRI system 40. For example, the MRI system 40 is adapted to carry out real-time MR image pulse sequence with support for device (e.g., catheter tip 14) tracking, following the principles first presented in an article by C. L. Dumoulin, S. P. Souza, and R. D. Darrow, entitled "Real-time position monitoring of invasive devices using magnetic resonance", Magnetic Resonance in Medicine, 1993, pp. 411-415, Vol. 29, and also described in U.S. Pat. No. 5,211,165 to Dumoulin, et al., entitled "Tracking system to follow the position and orientation of a device with radiofrequency field gradients", and such as found in more recent systems expanding upon the technique, for example, as described in a presentation by L. Pan, J. Barbot, S. M. Shea, et al., entitled "An Integrated System for Catheter Tracking and Visualization in MR-Guided Cardiovascular Interventions", The International Society for Magnetic Resonance in Medicine 2011, abstract 195, oral presentation, May 10, 2011, each of the three references being incorporated by reference herein. Also, the control processor 44b provides for control of the MR scanner 42, as well as for real-time feedback such as the ablation tip contact force measurement. It is noted that the MRI system 40 is adapted to operate with the catheter 10 and, to this end, the MRI system 40 may comprise appropriate components, for example, input/output devices, tangible data storage media, various software, graphical user interfaces, networking devices, etc.

Figure 4:
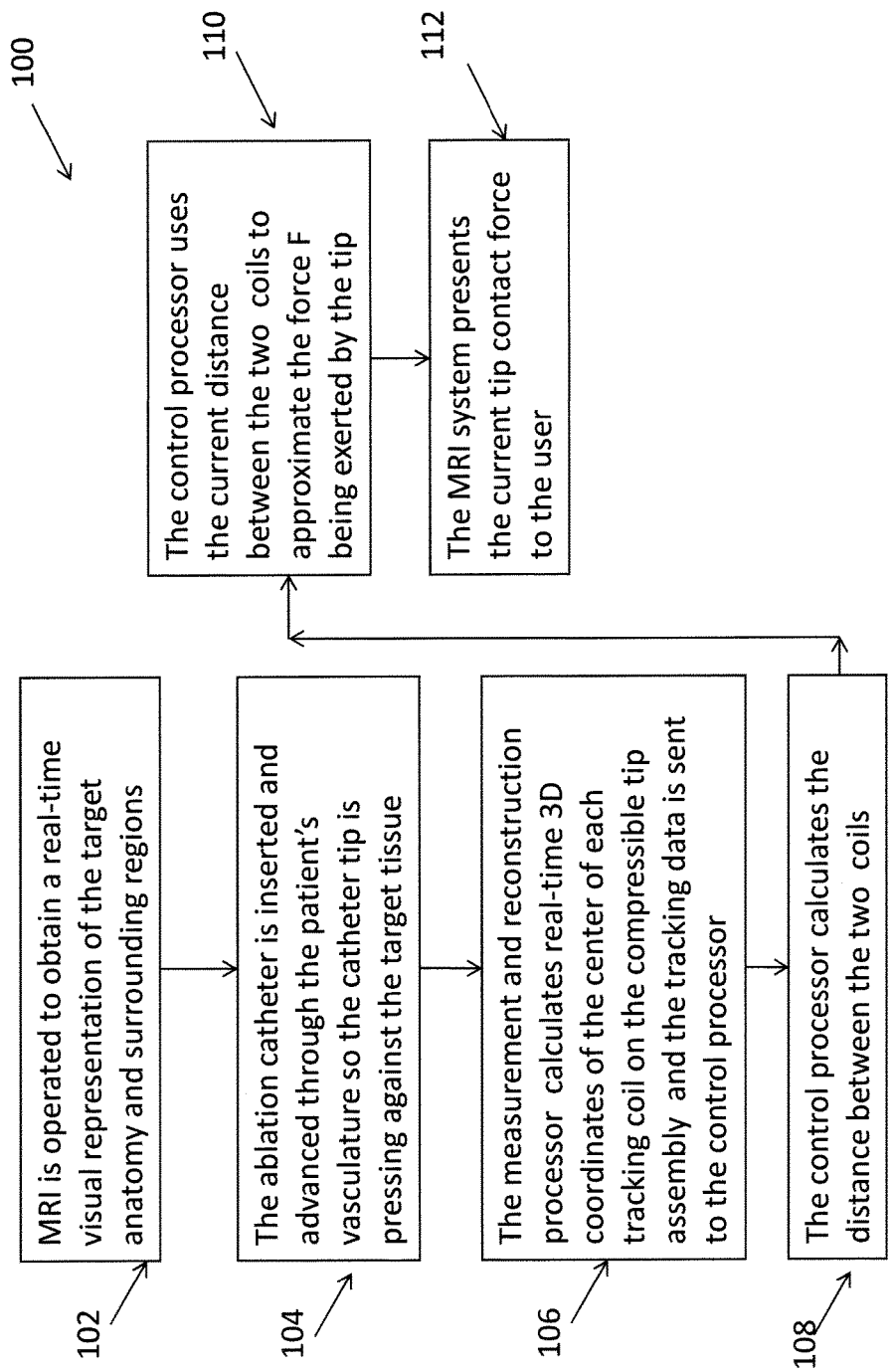
FIG. 4 is a block diagram of the operation of the integrated system of FIG. 3 in accordance with the present invention.

FIG. 4 is a block diagram of an operation 100 of the integrated catheter 10—MRI system 40 to measure the tip contact force during an interventional procedure. The procedure may be, for example, an RFA procedure in cardiac EP wherein a patient is undergoing an interventional procedure which involves the ablation catheter being in the proximity of a target anatomy (e.g., such as being inside the right atrium for a cardiac EP ablation procedure for the treatment of atrial fibrillation). In the first step 102, the MRI system 40 is operated to obtain a real-time visual representation of the target anatomy and surrounding regions. With the assistance of the imaging provided, the ablation catheter 10 is inserted and advanced through the patient's vasculature such that the catheter tip 14 is pressing against the target tissue (Step 104). This causes the compressible tip 14 to compress, moves the distal tip section 16 towards the proximal tip section 18, and decreases the distance between the two microcoils or tracking coils C1, C2 on the compressible tip assembly 14.

As part of the image reconstruction performed by the MRI system 40, the measurement and reconstruction processor 44a calculates real-time 3D coordinates of the center of each tracking coil, including the two tracking coils C1, C2 on the compressible tip assembly 14. This tracking data is sent to the control processor 44b (Step 106) to perform a force calculation. Specifically, the control processor 44b calculates the distance between the two compressible tip microcoils C1 and C2 (Step 108), given the relative x, y, z coordinates of each, using the following simple calculation for example:

$$\text{distance} = \text{square root } ((x2-x1)^2 + (y2-y1)^2 + (z2-z1)^2).$$

The control processor 44b then uses the current distance between the two compressible tip microcoils C1, C2 to approximate the force F being exerted by the tip 14 (Step 110), based on the known spring constant k and the following relationship:

$$F = k \cdot \text{delta},$$

where delta represents the total spring displacement and is equal to D_home−D_current+delta_initial delta; D_home represents the distance between the two microcoils C1, C2 in the "home state", when no force is exerted at the tip 14; D_current represents the current distance between the two microcoils C1, C2; and delta_initial represents the displacement of the spring in the "home state", relative to spring length under no compression.

Note that the above force calculation will benefit from higher accuracy in the MR tracking coil localization data. Expanding upon the original work by Dumoulin et al., as noted above, various work has been done aimed at improving this accuracy, including recent work described in a paper by J. Barbot, T. Wech, S. Shea, et al., entitled "Accurate Localization of Active Devices during Interventional MR Imaging", The International Society for Magnetic Resonance in Medicine 2011, 2011, p. 1747 and a paper by J. Barbot, S. Shea, K. Kirchberg, et al., entitled "Accurate Localization of Active Devices using Multi-scale Analysis for Interventional MR Imaging", The International Society for Magnetic Resonance in Medicine 2012, 2012, p. 5908, each of the two references being incorporated by reference herein.

The MRI system 40 may then present the current tip contact force to the user (Step 112). This may be done, for example, via a graphical display including a numeric readout and/or a graphical representation, that may include showing continuous gradations over the force range and/or indicating whether the force is in a minimal contact range, optimal contact range or an excessive contact range. The numeric and graphical display may also incorporate color ranges as additional cues as to which range the force is in. If the reconstruction algorithm implemented via the measurement and reconstruction processor 44*a* provides information as to the confidence of the current tracking data being reported, that confidence information may be incorporated into the contact force information being presented to the user, so as to give an indication of the accuracy of the force measurement.

Thus, the present invention offers a novel catheter and method of operation to measure contact force exerted by the catheter tip during an interventional procedure. As described above, the catheter comprises a catheter tip that has two sections with an RF tracking coil on each and a compression spring between the two sections. The method of operation to measure the contact force comprises deriving the 3D coordinates from the tracking coil signals to determine the distance between the two coils and in turn the amount of compression of the spring in the tip assembly (which can be interpreted into a force measurement, given the spring constant).

Advantageously, the contact force measurement is accomplished with the assistance of MRI-guidance using the MR tracking data which is already being generated to localize the catheter and catheter tip for visualization and navigation. MRI offers the general advantages of no ionizing radiation and better soft tissue imaging. While the better soft tissue imaging alone can offer enhanced image guidance, the use of an MRI-compatible catheter with tracking coils provides better visualization of the catheter position, taking the notion of "enhanced image guidance" a significant step further. Specific to cardiac RFA procedures, MRI can possibly provide imaging of lesions to assess the success of the ablations, which is more of an advantage in terms of procedural guidance, as opposed to real-time image guidance. This has been explored in recent work and is described in a paper by C. McGann, et al, entitled "Dark Regions of No-Reflow on Late Gadolinium Enhancement Magnetic Resonance Imaging Result in Scar Formation after Atrial Fibrillation Ablation," J Am Coll Cardio, 2011, pp. 177-185, Vol. 58, No. 2.

Figure 5:
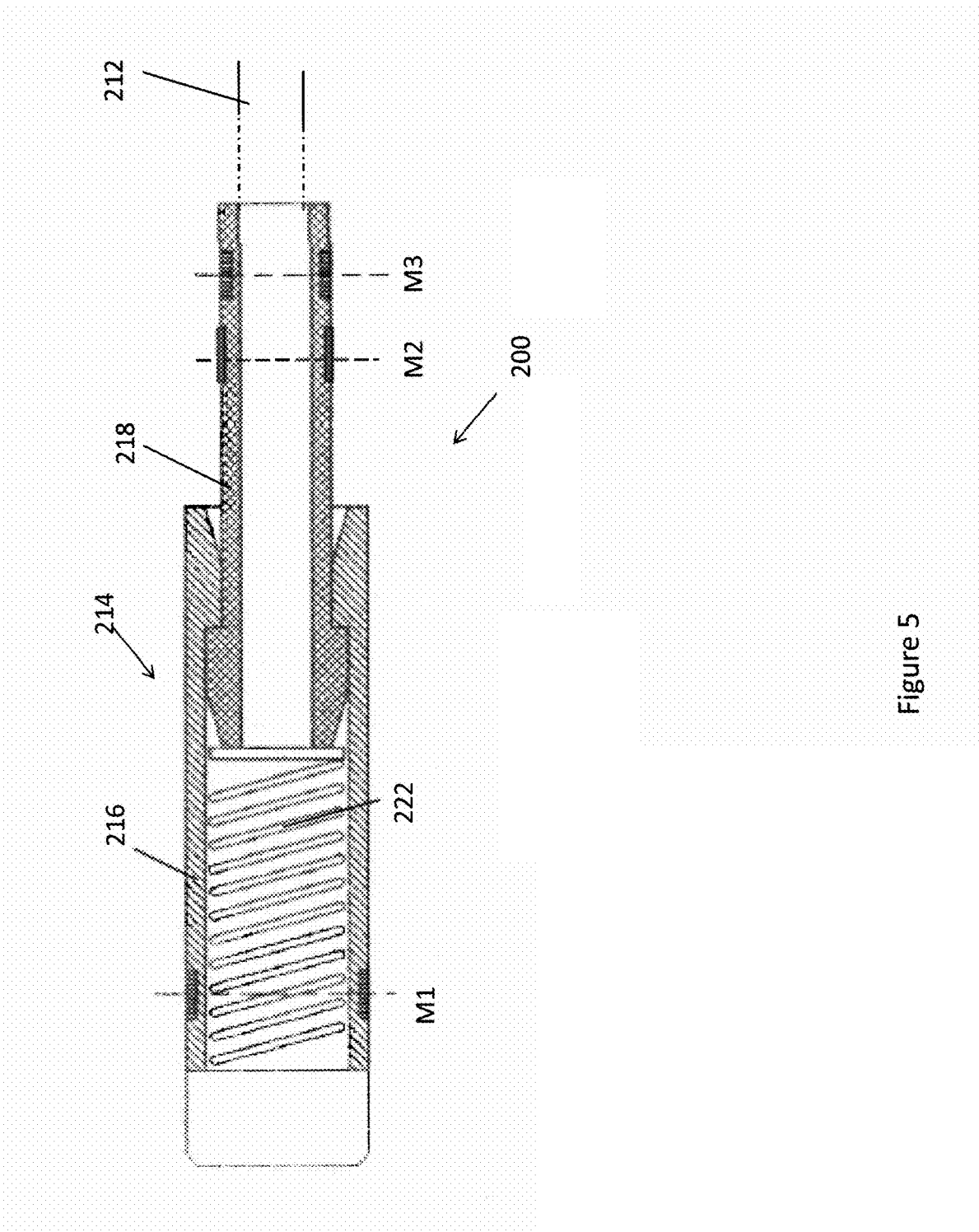
FIG. 5 is an illustration of a cross-section of a second catheter constructed in accordance with the present invention.

The present invention may also provide a catheter 200 that does not have support for device tracking via MR microcoil localization. Such a catheter 200 would provide the advantages of the first catheter 10, except those related to using MRI-guidance and MR tracking data. A cross-section of the alternative catheter 200 is shown in FIG. 5 and is alike the first catheter 10 in most respects of its construction and operation. For example, like the first catheter 10, the alternative catheter 200 comprises a catheter shaft 212, a compressible catheter tip 214 that has a distal tip section 216, a proximal tip section 218, and a compression spring 222 that is mounted inside the distal tip section 216, having a first end at the proximal end of the distal tip section 216, contacting the distal end of the proximal tip section 218, and a second end at the end of the distal tip section 216 opposite its proximal end, contacting an inside end wall of the distal tip section 216. However, neither the distal tip section 216 nor the proximal tip section 218 have an RF tracking coil incorporated into their respective outer walls. Instead, the two sections comprise passive markers M on their respective outer walls that may be detected by image processing.

The figure shows three markers, the 1st marker M1 being on the distal tip section 216 of the compressible tip 214 and the 2nd and 3rd markers M2, M3 being on the proximal tip section 218 of the compressible tip 214. All three markers M1, M2, M3 are positioned to be substantially collinear and to remain so during operation of the system 200 since, as noted above, the assembly of the two sections 216, 218 remains rigid in terms of having minimal flex of its longitudinal axis. The markers M1, M2. M3, although positioned to be collinear longitudinally, may be shaped to be partially annular or to partially follow the periphery of the respective outer wall (as shown on the figure). The distance between the 2nd and 3rd markers M2, M3, which are on the same section, remains fixed throughout any operation.

Like the first catheter 10, the alternative catheter 200 may be integrated with an image guidance system (not shown) to measure the tip contact force during an interventional procedure. The image guidance system may specifically use a projection imaging technique, such as a thick slice in MR imaging or a standard fluoroscopy projection, as long as the angle between the projection vector and the catheter tip 214 axis is not too small (e.g., at least 45 degrees). With such a guidance system, all three markers M1, M2, M3 will be distinctly visible in the projection and far enough apart from each other to be able to make reasonable measurements and derive respective force measurements.

So, for example, the projection imaging guidance system is operated to obtain a real-time visual representation of the target anatomy and surrounding regions and to assist in advancing the catheter 200 through the patient's vasculature to the target tissue. The compressible tip 214 compresses upon pressing against the target tissue, which moves the distal tip section 216 towards the proximal tip section 218 and decreases the distance between the 1st marker M1 and each of the other two markers M2, M3. From the marker positions determined in the respective 2D projection image, the actual distance between the 1st marker M1 and the 2nd marker M2 can be determined even if the tip 214 axis is foreshortened in the projection image because of the angle between the tip axis and the projection vector.

This may be generally accomplished as follows. The ratio of the distances between markers will be the same regardless of whether using actual distances or using foreshortened distances from the 2D projection image, for any angle between the tip axis and the projection vector. The following parameters may be defined for use in working with the distance ratios:

$da12$: current actual compressed distance between the 1st and 2nd markers M1, M2;

$da23$: fixed actual distance between the 2nd and 3rd markers M2, M3;

$dp12$: current distance between the 1st and 2nd markers M1, M2 in the 2D projection; and $dp23$: current distance between the 2nd and 3rd markers M2, M3 in the 2D projection.

The following distance ratios may then be defined:

$da12/da23 = dp12/dp23$, which may be rewritten as $da12 = da23 \cdot (dp12/dp23)$.

Since, as indicated above, the parameter da23 is a known, fixed distance, only the ratio of the distances from the 2D projection image is needed.

Thus, from a projection image of an arbitrary angle relative to the tip axis, the current actual distance between 1st and 2nd markers M1, M2 on the compressible tip assembly 214 may be determined. This is equivalent to the distance between the two microcoils C1, C2 in 3D space measured by the first catheter 10. Thereafter the force approximation/calculation based on the spring constant is the same as performed by the first catheter 10 (described above).

In this 2D projection imaging approach using the alternative catheter 200, the identification of the marker positions may be done by a measurement and reconstruction processor of the image guidance system, or alternatively, in an additional software module of the system analyzing the 2D images produced by the reconstruction. Various forms of reconstruction may be used since this approach may utilize different projection imaging techniques other than MR imaging.

Note that the restriction for the alternative catheter 200 that the angle between the tip axis and the projection vector not be too great may be easily solved by the respective image guidance system (and/or alternative catheter 200) use of an algorithm to automatically make iterative adjustments to the projection vector. If the parameter dp23 increases per the projection angle change, that is an improvement. If parameter dp23 decreases per the projection angle change, the opposite angle change should be made.

The operation of the alternative catheter 200 may be further automated. For example, the measurement and reconstruction processor 44a may determine that da23<da12 even at the maximum compression of the spring 222. In such case, the measurement and reconstruction processor 44a may correspond the parameter dp23 to the marker pair having the shortest distance between them, the longest distance being between the 1st and 3rd markers M1, M3. This will enable the catheter-image guidance system to easily determine the identity of each marker, M1, M2 and M3.

It is noted that patents exist for ablation catheters which employ some sort of spring in the catheter tip. In one patent, U.S. Patent Publication 2010/0121269 to Goldenberg et al., entitled "Apparatus and method for sensing force on a robotically controlled medical instrument", the spring is incorporated in the sensor in the tip. In U.S. Pat. No. 7,311,704 to Paul, et al., entitled "Spring-tip, flexible electrode catheter for tissue ablation", the spring is involved as a more integral part of the actual ablation electrodes at the tip. In U.S. Pat. No. 5,255,679 to Imran, entitled "Endocardial catheter for mapping and/or ablation with an expandable basket structure having means for providing selective reinforcement and pressure sensing mechanism for use therewith, and method", the spring is involved in the transmission of the contact force back to the control handle. In distinct contrast, the present invention provides a catheter tip that is adapted to have deflection of an associated spring detected by imaging techniques and to have that deflection be translated into an estimation of the tip contact force.

It is also noted that the present invention provides several further advantages in addition to those already described. For example, no additional sensors or associated wires or fibers are needed for a respective catheter system. Further, force is stored in the compressible tip's spring, assuring that the contact force remains more uniform as the catheter and patient anatomy both move, and decreasing lapses in contact force. In occurrences of excessive device (e.g., catheter) or anatomy movement as might cause excessive contact force and possibly patient injury, the compressible tip will act as a buffer, effectively decreasing the contact force to some degree (via the action of the spring compressing to absorb some of the excessive contact force). The present invention may also be incorporated into a system which uses fiber-optic or other such force sensors, serving as a back-up or secondary force measurement, as could be particularly useful for systems with a high risk of excessive force, such as medical interventional robotic systems.

Other modifications are possible within the scope of the invention. For example, the subject patient to be scanned may be a human subject, animal subject or any other suitable object. Also, there may be alternative designs of the compressible catheter tip 14 and/or the associated spring 22 that may be used by the present invention. Also, the present invention may be used for other medical interventional applications having a need for force sensing, besides the cardiac EP domain, as well as for non-medical applications having a need for force sensing.

Also, in further automating the operation of the alternative catheter 200, the measurement and reconstruction processor 44a may determine that da23>da12 even at the maximum compression of the spring 222. In such case, the measurement and reconstruction processor 44a may correspond the parameter dp12 to the marker pair having the shortest distance between them.

Also, although the steps of the method 100 have been described in a specific sequence, the order of the steps may be re-ordered in part or in whole and the steps may be modified, supplemented, or omitted as appropriate. Also, the method 100 may use various well known algorithms and software applications to implement the steps and substeps. Further, the method 100 may be implemented in a variety of algorithms and software applications. Further, the method 100 may be supplemented by additional steps or techniques. It is also understood that the method 100 may carry out all or any of the steps using real-time data, stored data from a data archive or database, data from a remote computer network, or a mix of data sources.

Also, the various described instrumentation and tools may be configured and interconnected in various ways as necessary or as desired. Further, although in the described method 100 the user may use self-contained instrumentation and tools, the user may use other instrumentation or tools in combination with or in place of the instrumentation and tools described for any step or all the steps of the method 100, including those that may be made available via telecommunication means. Further, the described method 100, or any steps, may be carried out automatically by appropriate instrumentation and tools or with some manual intervention.

The invention claimed is:

1. A catheter comprising
a compressible catheter tip that includes a moveable distal tip slidably connected to a fixed proximal tip and a plurality of markers,
wherein at least one of said plurality of markers is positioned on the moveable distal tip and at least one of said plurality of markers is positioned on the fixed proximal tip,
wherein the plurality of markers are adapted to permit an external image guidance system to track the markers, to obtain positional information of the markers, and to estimate contact force of the tip from the positional information.

2. The catheter of claim 1, wherein the markers are adapted to permit the associated image guidance system to measure a deflection of the tip for estimating contact force of the tip.

3. The catheter of claim 1, wherein the compressible catheter tip further has a compression spring incorporated inside moveable distal tip and in contact with an end of the fixed proximal tip, and
the markers are adapted to permit the associated image guidance system to measure a deflection of the compression spring for estimating contact force of the tip.

4. The catheter of claim 1, wherein the markers comprise magnetic resonance tracking coils incorporated in a structure of the tip.

5. The catheter of claim 4, wherein
the image guidance system performs magnetic resonance imaging to track the coils and to obtain 3-dimensional (3D) positional information of the coils.

6. The catheter of claim 1, wherein the markers comprise passive markings on an exterior surface of the tip.

7. The catheter of claim 6, wherein
the image guidance system performs projection imaging to track the markings and to obtain 2-dimensional (2D) positional information of the markings.

8. A system that integrates a catheter system and an image guidance system, comprising
a compressible catheter tip that includes two sections slidably connected to one another and a plurality of markers, wherein each section includes at least one of the plurality of markers,
wherein the plurality of markers provide localization of a catheter tip for visualization and navigation by the imaging guidance system and provide a measure of a deflection of the catheter tip for estimating tip contact force by the imaging guidance system.

9. The system of claim 8, wherein the markers comprise magnetic resonance tracking coils incorporated by a structure of the catheter tip and
the image guidance system comprises a magnetic resonance imaging system.

10. The system of claim 9, wherein the compressible catheter tip comprises
a compression spring connected between the two sections, and
the image guidance system derives 3-dimensional (3D) coordinates from tracking coil signals to determine a distance between the two coils and estimate tip contact force from an amount of compression of the spring.

11. The system of claim 8, wherein the markers comprise passive markings on an exterior of the catheter tip and
the image guidance system performs projection imaging.

12. The system of claim 11, wherein the compressible catheter tip comprises
a compression spring connected between the two sections, and
the image guidance system derives 2-dimensional (2D) coordinates from the passive markings to determine the distance between the two markings and estimates tip contact force from an amount of compression of the spring.

13. The system of claim 8, wherein the compressible catheter tip comprises
a compression spring connected between the two sections, wherein
one section has a passive marking on a respective surface and the other section has at least two passive markers on a respective surface, and
the image guidance system derives 2-dimensional (2D) coordinates from the passive markings to determine a distance between a marking on one section and a marking on the other section and estimate tip contact force from an amount of compression of the spring.

14. The system of claim 13, wherein the at least two passive markers on the other section have a respective fixed and predetermined distance between a respective pair.

15. A method of measuring the contact force exerted by a catheter tip against a target object, comprising
deriving respective positional coordinates of each of a plurality of markers on the catheter tip during operation of the catheter tip;
determining the respective distance between the markers during operation of the catheter tip; and
calculating a contact force of the tip against the target object,
said catheter including a moveable distal tip slidably connected to a fixed proximal tip wherein at least one of said plurality of markers is positioned on the moveable distal tip and at least one of said plurality of markers is positioned on the fixed proximal tip to provide a variable distance between at least two of the plurality of markers during operation of the catheter tip.

16. The method of claim 15, wherein the catheter comprises an associated compression spring to provide said variable distance between at least two of the plurality of markers during operation of the catheter tip and
the calculating step comprises calculating contact force of the tip against the target object based on the spring's properties.

17. The method of claim 15, wherein the deriving step comprises obtaining respective 3-dimensional (3D) coordinates of each of the plurality of markers from real-time localization and visualization from magnetic resonance imaging of the catheter tip and the markers.

18. The method of claim 15, wherein the deriving step comprises obtaining respective 2-dimensional (2D) coordinates of each of the plurality of markers from real-time localization and visualization from projection imaging of the catheter tip and the markers.

19. A method of magnetic resonance (MR) imaging guidance of a medical interventional procedure, comprising
localizing MR tracking coils incorporated in a catheter used in a respective procedure and
measuring catheter tip force from a localization information during MR image visualization of the patient anatomy under examination, wherein
said catheter includes a moveable distal tip slidably connected to a fixed proximal tip and a plurality of markers, wherein at least one of said plurality of markers is positioned on the moveable distal tip and at least one of said plurality of markers is positioned on the fixed proximal tip.

20. The method of claim 19, wherein the catheter is adapted to provide a variable distance between at least two of the MR tracking coils during the respective procedure.

21. The method of claim 19, further comprising
presenting force measurement for the respective procedure that indicates an accuracy of the force measurement.

* * * * *